United States Patent [19]

Watson et al.

[11] Patent Number: 4,887,600
[45] Date of Patent: Dec. 19, 1989

[54] USE OF LASERS TO BREAK DOWN OBJECTS

[75] Inventors: Graham Watson, London, England; Horace Furumoto, Wellesley, Mass.

[73] Assignee: The General Hospital Corporation, Boston, Mass.

[21] Appl. No.: 41,158

[22] Filed: Apr. 22, 1987

Related U.S. Application Data

[63] Continuation-in-part of Ser. No. 726,472, Apr. 24, 1985.

[30] Foreign Application Priority Data

Apr. 22, 1986 [IL] Israel ........................................ 78567

[51] Int. Cl.$^4$ ............................................ A61B 17/00
[52] U.S. Cl. ........................................ 606/128; 606/15
[58] Field of Search ........................................ 128/4–8, 128/303.1, 395–398, 24 A, 328

[56] References Cited

U.S. PATENT DOCUMENTS

3,890,578  6/1975  Wang ............................ 331/94.5 L
4,608,979  9/1986  Breidenthal et al. ............ 128/303.1
4,784,135  11/1988  Blum et al. ..................... 128/303.1

FOREIGN PATENT DOCUMENTS

WO85/03631  2/1985  European Pat. Off.
2538960  9/1975  Fed. Rep. of Germany.

OTHER PUBLICATIONS

"Lithotomy of Intrahepatic and Choledochal Stones with Yag Laser", Orii et al. Apr. 1983 Surg. Gyn. & Obstetrics.
"The Laser Beam in Urology", Mulvaney et al. The Jrl. of Urology 1968.
"Disintegration of Urinary Calculi by Laser Beam: Drilling Experiment in Extracted Urinary Stones", Tanahashi and Orikasa & Chiba 1979.
"Transurethral Disintegration of Urinary Calculi by the Use of Laser Beam", Tanahashi and Numata et al., Urology 1982.
"In Vitro Destruction of Urinary Calculi by Laser-Induced Stress Waves", Fair, Medical Instr. 1978.
"Laser Fragmentation of Renal Calculi", Watson et al. British Jnl. of Urology 1983.
"The Use of Laser Beam in Urology", Tanahashi and Orikasa, 1979.
Mulvaney, W. P. and C. W. Beck, J. Urology, 99, 112–115 (1968).
Fair, H. D., Medical Instrumentation, 12:100–106 (1978).
Tanahashi, V. et al., Tohoku J. Exp. Med., 128:189–196 (1979).
Tanahashi et al., "Transurethral Disintegration of Urinary Calculi . . . " (1980).
Watson, G. et al., British J. Urology, 55:613–616 (1983).
Watson, G. M., "Laser Fragmentation of Renal and Biliary Calculi", in Lasers in Medicine and Surgery (Dec. 13, 1983).
Watson et al., "Tunable Pulsed Dye Laser for Fragmentation of Urinary Calculi" in Lasers in Surgery and Medicine (Apr. 15, 1985; Abstracts 82 and 163).

Primary Examiner—Max Hindenburg
Attorney, Agent, or Firm—Hamilton, Brook, Smith & Reynolds

[57] ABSTRACT

Calculi, stones, calcified tissue and other material are broken down for removal from within a body using laser pulses that are delivered via an optical fiber and have a wavelength, intensity, energy per pulse and pulse duration selected to break down the object into smaller particles without delivering energy sufficient to cause damage to other tissue.

35 Claims, 3 Drawing Sheets

USE OF LASERS TO BREAK DOWN OBJECTS

RELATED APPLICATIONS

This is a continuation-in-part of application Ser. No. 726,472, filed Apr. 24, 1985 and entitled "Use of Lasers to Break Down Objects," still pending.

BACKGROUND

This invention relates to using a laser beam delivered via an optical fiber to break down a calculus, stone or calcified tissue or other material for removal from within the human body.

Frequently such calculi, stones, or calcified tissue are located in positions which can be reached using only small diameter endoscopes and the optical fiber must be fine enough to pass via the endoscope. The stones are typically in close proximity to healthy tissue.

SUMMARY OF THE INVENTION

The general feature of the invention is in delivering via the optical fiber laser pulses having a wavelength, energy, intensity and pulse duration which will break down the calculus, stone, calcified tissue or other material into smaller particles without delivering energy sufficient to cause damage to other tissue in the same vicinity.

The material to be removed from the body is illuminated in a localized region with a pulsed laser. By surrounding the material with liquid and illuminating the localized region with light above a threshold intensity level, a shock wave can be generated from the localized region. It is believed that the shock wave fragments the materials beyond the localized region even though heating is limited to the localized region.

Thus, the stone is safely and relatively quickly broken down into easily removed sand-like particles, without melting. Thermal damage to surrounding tissue is limited. The stone and the particles are not propelled into the surrouding tissue. Degradation of the optical fiber by the laser beam is limited. The fiber can be sufficiently small in diameter to be useful with small diameter endoscopes.

The preferred embodiments include the following features. The pulses are at wavelengths corresponding to wavelengths for which the object has a relatively shallow depth of penetration. Preferably wavelengths between 350 and 550 nanometers are used for urinary calculi (most preferably 251, 504, or 450 nanometers). The laser is preferably of the pulsed dye type for relatively long pulse durations but may be of other types. The pulses have durations of at least 10 nanoseconds (preferably between 0.05 and 2 microseconds), and the pulse energy is no greater than 0.200 joules, preferably between 0.005 and 0.200 joules. The fiber is flexible and has a core diameter no greater than 1000 microns, preferably between 60 and 600 microns, and more specifically 200 microns. The distal end of the fiber is in contact with the object (a stone) and the interface between them is surrounded by fluid. The laser pulses are applied in brief bursts, preferably greater than 10 hertz, and remaining fragments are broken down by one-shot pulses.

Other advantage and features of the invention will become apparent from the following description of the preferred embodiment, and from the claims.

DRAWINGS

DESCRIPTION OF THE PREFERRED EMBODIMENTS

Figure 1:
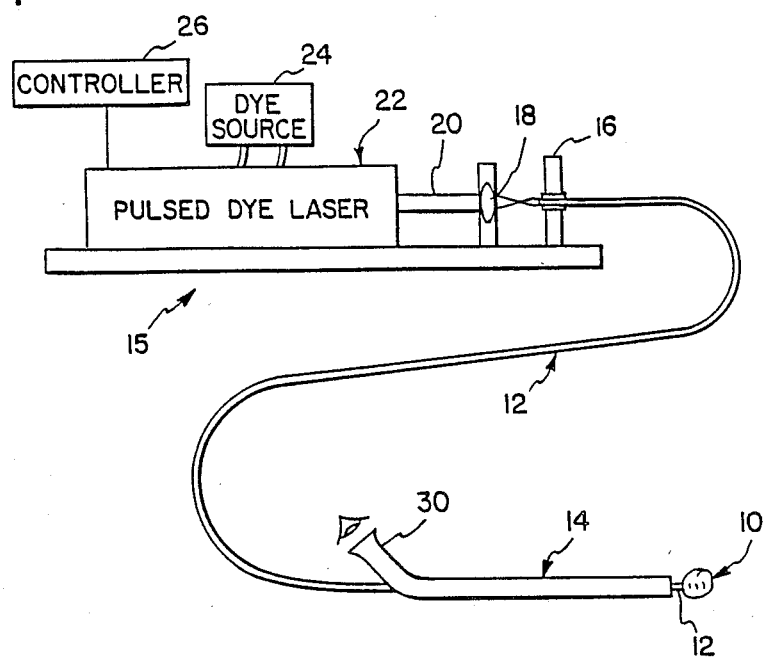
FIG. 1 is a diagram of a system for breaking down unwanted objects or tissue.

Referring to FIG. 1, a urinary calculus (stone) 10 to be removed from within a human body is contacted by the cleaved distal face of a flexible quartz silica optical fiber 12 (Superguide series available from Fiberguide Industries) having a core diameter in the range of 60 to 400 microns. Fiber 12 passes through a ureteroscope 14 and extends to a laser source 15, where the proximal face of fiber 12 is held in a fiber mount 16 (Model FP2 available from Newport Corporation). The proximal face of fiber 12 is exposed to receive, via a convergent lens 18, (of appropriate focal length for the fiber), a beam 20 from a linear flash lamp pumped pulsed dye laser 22. Laser 22 is connected to a source 24 of dye of a selected wavelength characteristic. Laser 22 is also connected to a controller 26 which includes a control panel to permit the user to activate and deactivate the laser and to vary the pulse energy and pulse repetition rate of the laser beam. Laser 22 and controller 26 are available from Candela Corporation, Natick, Massachusetts.

Ureteroscope 14 includes an eyepiece 30 through which the user can observe the stone and the distal end of the fiber, as well as a light source (not shown) to illuminate the distal end for viewing and an irrigation lumen to deliver an irrigant to the distal end.

The wavelength at which the laser will be operated (and hence the dye to be used) is chosen in part on the basis of the percentage transmission characteristics of the stone material. For example, the percentage transmission of calcium phosphate and calcium oxalate stone materials for different wavelengths was measured experimentally (by conventional spectroscopy) on sections of dry stones which were sanded to form progressively thinner wafers. The resulting graph of the log of the percentage transmission against thickness was linear indicating the following 1/e depths of penetration for different wavelengths.

| | 1/e Depth of Penetration (mm) | |
|---|---|---|
| Wavelength (nm) | Calcium Phosphate | Calcium Oxalate |
| 1064 | 2.16 ± 0.8 | 3.58 ± 0.85 |
| 577 | 0.81 ± 0.2 | 0.50 ± 0.1 |
| 504 | 0.54 ± 0.05 | 0.30 ± 0.2 |
| 450 | 0.42 ± 0.05 | 0.24 ± 0.05 |
| 308 | 0.25 ± 0.03 | 0.18 ± 0.1 |

The penetration depth decreases with shorter wavelengths. The smallest penetration depth is the most desirable from the point of view of enabling a low energy threshold to accomplish fragmentation, producing small-size fragments, and limiting the propulsion of fragments into surrounding tissue. Very short wavelengths (shorter than 350 nm) in the ultraviolet range (for example 308 nm), however, are known to be mutagenic and are difficult to deliver via the optical fiber and therefore are avoided. Wavelengths in the range 450 to 550 nanometers are preferred. Dyes are available which operate at the 450 nm (blue) and 504 nm (green) wavelengths. The 450 nm dye fades fairly rapidly. Where the cost of the dye is an issue, the best choice is the 504 nm dye.

Figure 2:
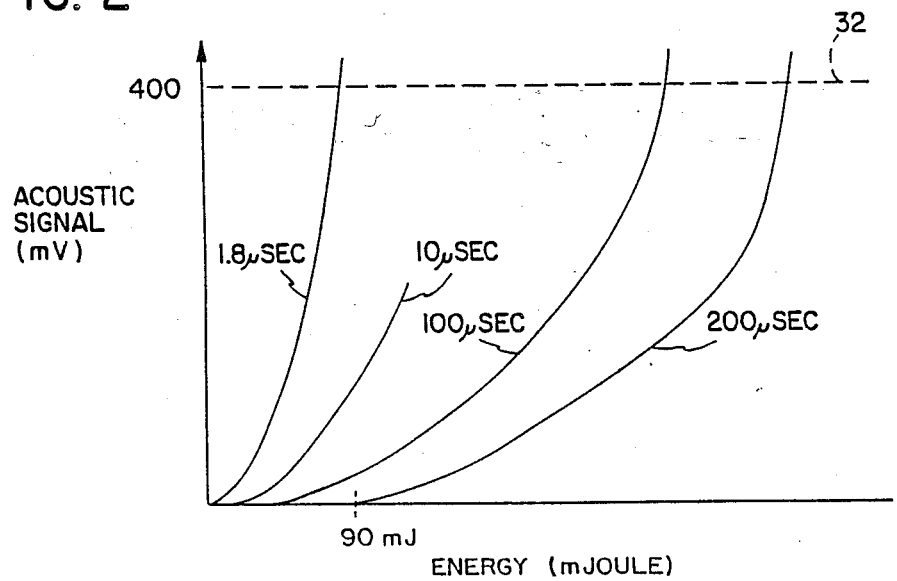
FIG. 2 is a family of curves showing fragmentation thresholds versus pulse energy for different pulse durations.

The duration of each pulse delivered by the laser is chosen to minimize the energy delivered to the stone while still accomplishing fragmentation (i.e., the breaking down of the stone into smaller particles). Referring to FIG. 2, the threshold energy in millijoules per pulse required to initiate fragmentation of an oxalate stone for a given pulse duration at 577 nm using a 600 micron optical fiber was determined experimentally by measuring an acoustic signal in the stone resulting from the pulse. The acoustic signal was measured electronically in millivolt units. Dashed line 302 represents the acoustic level (nominally 400 millivolts) which corresponds to the initiation of fragmentation in a stone. Each curve represents, for a given pulse duration, the variation of acoustic signal with energy per pulse. The point at which each curve crosses line 30 is the threshold pulse energy level at which fragmentation will occur. The threshold energy level decreases with decreasing pulse duration. Because lower energy pulses are less likely to cause thermal damage or to propel the stone or the broken off particles into surrounding tissue, pulse durations of less than 10 microseconds, preferably between 0.05 and 2.0 microseconds, are used.

Figure 3:
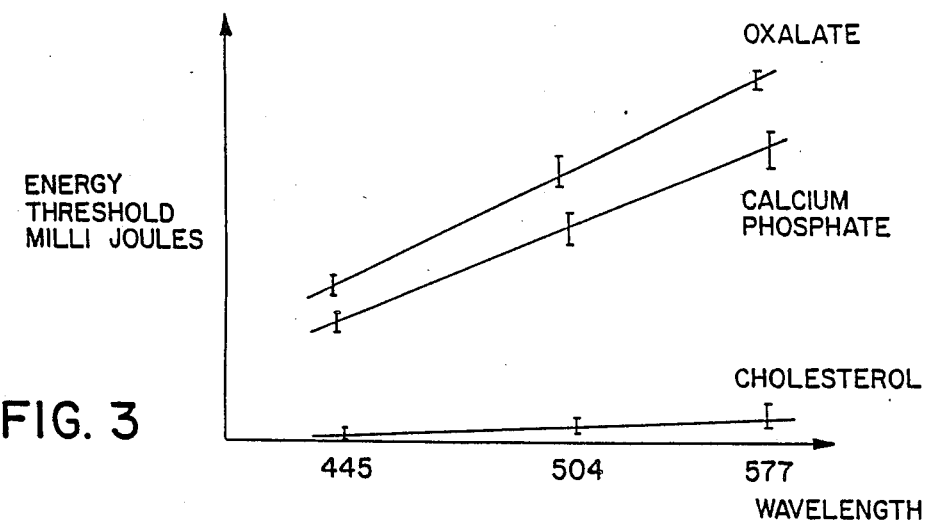
FIG. 3 is a family of curves indicative of fragmentation threshold pulse energy vesus wavelength for different types of stones.

Referring to FIG. 3, the pulse energy threshold for causing an acoustic signal at a given level (25 millivolts) was determined for three different stone types at three different wavelengths, further confirming the desirablility of using shorter wavelengths regardless of the stone material.

Figure 4:
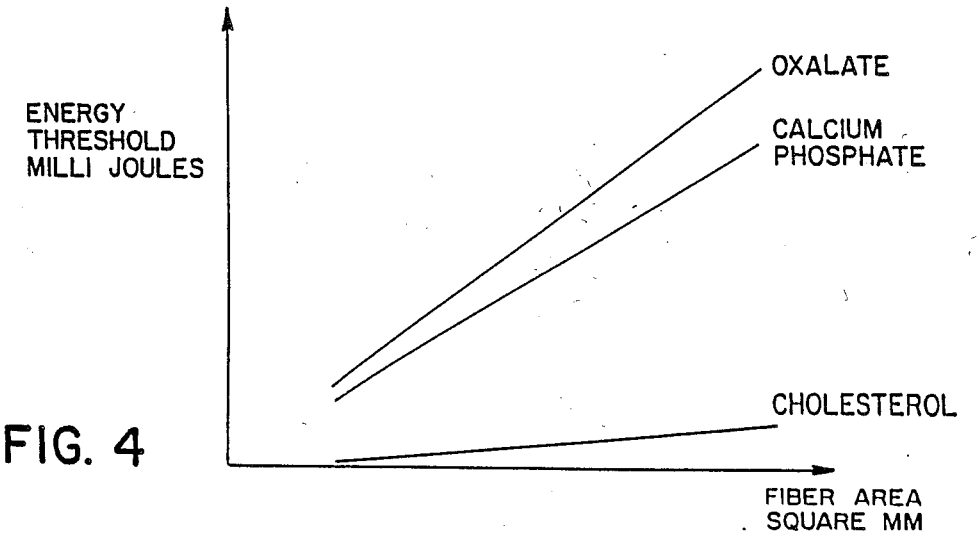
FIG. 4 is a family of curves indicative of fragmentation threshold pulse energy versus fiber area for different types of stones.

Referring to FIG. 4, the relatationship between cross-sectional area of fiber 12 and the threshold pulse energy required to cause an acoustic signal at the 25 mv level was determined for three different stone materials. In all cases the threshold pulse energy decreases linearly with fiber area. Different fiber sizes have been used: 1000, 600, 400, 200, 100 and 60 microns.

Figure 5:
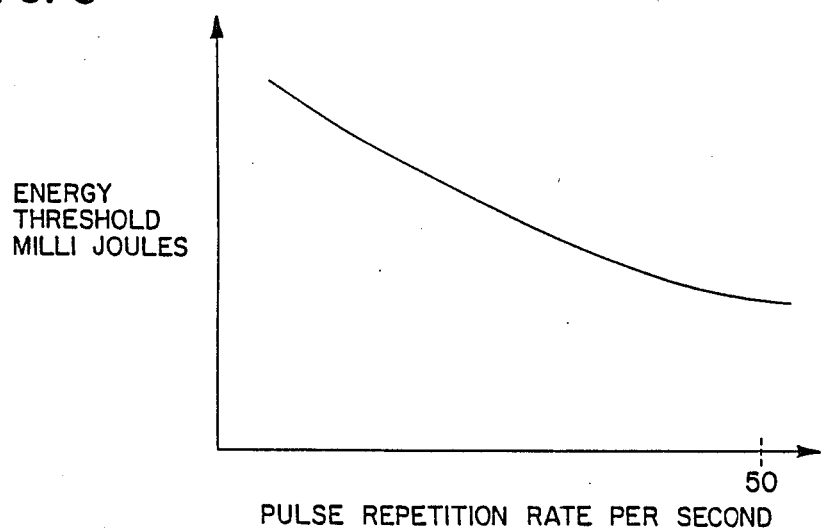
FIG. 5 is a curve indicative of fragmentation threshold pulse energy versus pulse repetition rate.

The pulse repetition rate may also be chosen to reduce the threshold pulse energy at which fragmentation is expected to occur. Referring to FIG. 5, the energy required to produce the 25 mv acoustic signal decreased with increasing pulse repetition rate. Furthermore, at higher repetition rates, the fragmentation proceeds more rapidly. At higher repetition rates, however, the dye is depleted faster and the optical fiber is less capable of passing the energy to the stone. A maximum practical rate is not much greater than 100 Hertz and the optimum rate is about 20 Hertz.

It can be shown experimentally that above the energy pulse threshold, the average weight of fragments yielded per pulse increased sharply and that laminated oxalate stones have a substantially lower fragmentation threshold than do homogeneous oxalate stones. Thus the pulse energy can be varied to break down different stones.

Operation

In operation, after inserting the ureteroscope 14 to reach the site at which the stone 10 is located, the distal end of the fiber 12 is inserted through the ureteroscope and oriented by sight, so that the distal face of the fiber is in contact with the stone 10. The site is irrigated via a lumen in the ureteroscope so that the stone is surrounded by liquid. The laser is set at a wavelength between 450 and 550 nanometers by selecting an appropriate dye. The pulsed dye laser controller 22 is adjusted to set the pulse energy and pulse repetition rate. The laser pulse energy is initially set at a value which is lower than the threshold fragmentation level and then increased until the desired fragmentation effect has been attained. Preferably the pulsed dye laser is operated at about 30 millijoules per pulse for a 200 micron fiber and about 100-150 millijoules per pulse for a 600 micron fiber, and in no event more than about 200 millijoules. The pulse repetition rate is set between 10 and 50 Hertz.

Figure 6:
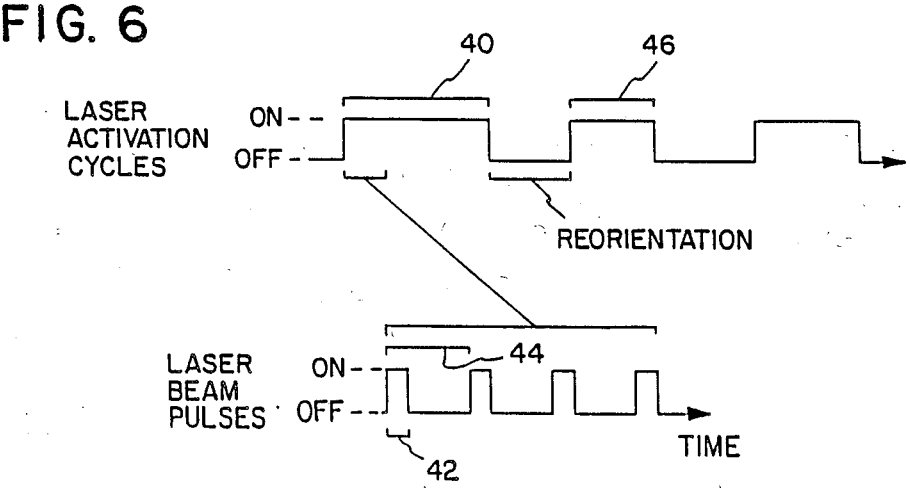
FIG. 6 is a diagram of pulse timing.

Referring to FIG. 6, the laser 22 is activated for a brief burst, for example for a period of a second or a fraction of a second (identified as 40 in FIG. 6). The laser pulse duration 42 is typically between 0.1 and 2.0 microseconds. The period of the pulse repetition is identified as 44 on FIG. 6. During activation period 40, a portion of the stone breaks down into a combination of vapor and sand-like particles small enough to be easily removed.

The distal face of the fiber is then reoriented (during a period identified as reoriented in FIG. 6) to be once again in contact with the stone. Then the laser is again activated briefly for a burst period 46, to cause another portion of the stone to break down. The process is repeated until the entire stone has been broken down. Any fragments which need to be broken down further can then be broken down by touching them with the distal end of the fiber and applying a single shot laser pulse.

The stone is safely and relatively quickly broken down into easily removed sand-like particles, without melting. Thermal damage to surrounding tissue is limited. The stone and particles are not propelled into the surrounding tissue. Degradation of the optical fiber by the laser beam is limited. The fiber can be sufficiently small in diameter to be useful with small diameter endoscopes.

Other embodiments are within the following claims. For example, although less desirable, laser 22 can be an excimer laser tuned to a particular wavelength by a selected gas mixture. The wavelength is chosen to be as short as possible while still permitting the pulses to be delivered via the optical fiber. Preferably the gas mixture is xenon-fluoride providing a wavelength of 351 nm. The resulting pulses have very shallow penetration into the stone and operate to break the stone into extremely fine particles and vapor. Progress through the stone is slower per pulse than for the pulsed dye laser, but this is offset by higher pulse repetition rates which are possible with the excimer laser. The pulse durations typical of excimer lasers are 10 nanoseconds but can be lengthened by various techniques to 80 or more nanoseconds. Such pulse durations make the pulses somewhat more difficult to deliver via the optical fiber than the pulsed dye laser pulses.

Using the excimer laser on an oxalate calculus via a 1000 micron fiber at 351 nm, a repetition rate of 200 Hertz, and a pulse energy of 30 millijoules (energy density of 1.6 joules/cm ), produced an average yield of fragments per pulse of 10 micrograms. By comparison, using the pulsed dye laser at 450 nm and a pulse energy of 20 joules/cm via a 600 micron fiber generated 100 micrograms of fragments per pulse. Using the pulsed dye laser at 504 nm at a pulse energy of 25 joules/cm via a 600 micron fiber yielded 1 milligram per pulse.

The product of breaking down the stone is about 90% vapor for the excimer laser and 10% for the pulsed dye laser.

In other embodiments, gallstones or arterial plaque may be broken down by a pulsed dye laser at 450 nm, and any appropriate technique for reaching the stone with the distal end of the fiber may be used.

The following describes observations made in the process of breaking down calculus, stone and calcified tissue using a laser.

1. Laser radiation is absorbed by the target material at wavelengths characteristic of its absorption spectra. Laser light of shorter wavelengths is better for white or translucent material.

2. The laser intensity must be greater than a certain level before a significant effect is observed. The intensity is proportional to the energy delivered and inversely proportional to the pulse duration of the laser, and the distal end of the fiber must touch or be in close proximity to the target for maximum effect. However, a fiber is not necessary inasmuch as the same effect can be obtained by focusing the laser beam on the target so that the intensity threshold is reached.

3. When the threshold for breakdown is reached, a loud acoustic signal is heard. The target material must be completely immersed in liquid for maximum breakdown. A wetted target or a target slightly below the surface of the liquid (2 or 3 mm) will give a loud acoustic signal but will not readily break down the target.

It is believed that the fragmentation process is as follows:

1. The laser radiation is first absorbed by the target. For white or translucent material, shorter wavelengths are preferred.

2. A minimum laser threshold intensity (power per unit area) is necessary to vaporize, heat and ionize the target.

3. The laser energy is confined in a small volume by a surrounding liquid. Increasing the energy density as more laser light is absorbed increases the pressure in the volume to several hundred kilobars. At such pressures, shock waves with average velocities over 0.5 mm per microsecond can be formed. "Laser Induced High Pressure Shock Waves in Water", C. E. Bell and J. A. Landt, Applied Physics Letters 10, 46 (1966) and "Intense Ruby Laser Induced Acoustic Impulses", E. F. Carame, C. E. Moeller and N. A. Clark, Jrn of Acoustical Soc of America 40, 1463 (1966).

4. The spherical shock wave is propagated into the calculus, stone or calcified tissue to break it down. The liquid is necessary to confine the interaction volume so that a high pressure shock is generated. The liquid also helps to couple the shock wave into the target. If the target is only wetted or submerged slightly, the interaction volume expands so that only a moderate to weak shock is generated which will not break down the target.

There are several considerations in the optimization of the use of lasers to break down objects for removal from within the body. They are energy per pulse, intensity (power density), pulse duration, repetition rate, color, fiber size, and fiber damage level. These considerations are not independent of each other. In addition, treatment time should be shortened whenever possible and risk of damage to living tissue in the body should be minimized.

1. Energy per pulse. Energy per pulse should be as large as possible to maximize the amount of material to be broken down in the shortest period of time.

2. Fiber size. Small fibers are preferred because they are more flexible and because endoscopes or catheters composing the delivery systems can be made smaller. Fibers over 600 microns in diameter are too large, while fibers smaller than 60 microns will not be able to transmit much total power or energy, thereby increasing treatment time. One to two hundred micron fibers are considered optimum.

3. Intensity. The laser intensity out of the fiber must be high enough to form a shockwave at the target. This effect has a threshold which has been shown to be 5 megawatts per square centimeter. An intensity of at least 10 megawatts per square centimeter is preferred. The area of the spot is determined by the fiber cross section. The highest intensity occurs when the fiber touches the target and intensity is quickly reduced as the fiber is withdrawn from contact. A lens system to focus the light from the fiber on to the target to obtain the desired intensity is conceivable but difficult to reduce to practice. Furthermore, the shock generated erodes the fiber tip. This is not too serious for the distal surace of the cleaved fiber tip but is a serious effect for a lens unless the lens is far removed from the focus.

4. Pulse duration. Total power for a given energy can be increased by reducing pulse duration. Typical Q switched, excimer or nitrogen lasers will have pulse durations in the order of 1 to 20 nsec. The damage intensity for quartz fiber is about 300 to 400 megawatts per square cm. A 400 micron fiber will transmit approximately 10 mj in a 20 nsec pulse at the damage level provided that the laser uniformly illuminates the fiber. However, the laser beam must be focused into the fiber and peak intensity spots will limit the total energy to a few millijoules. Higher energy throughput is desired for rapid treatment.

Longer pulses of at least 0.05 microseconds, and preferably greater than the 0.1 microseconds available with dye lasers, allow more energy to be transmitted for a given fiber size. However, too long a pulse will allow the interaction volume to expand and the shock to dissipate. For high pressure shocks in liquids, a pulse duration 2 microseconds or less is desired.

5. Repetition rate. The higher the setting of the repetition rate, the faster is the treatment. However, single shot capacity is also necessary to further fragment small broken off particles.

Table I sets forth the optimized operating ranges for various treatments. A flashlamp excited dye laser can be designed to perform at the optimum conditions for each of the listed treatments.

A less desirable embodiment is the use of an excimer, gold or copper vapor, frequency doubled repetitively switched YAG or a nitrogen laser for laser 22. These lasers have higher peak output powers and shorter pulse durations than a flashlamp excited dye laser and the fiber damage threshold of 400 MW/cm is reached at relatively low energy. The higher intensity requires the use of larger diameter fiber to prevent damage to the fiber and allows for even larger diameter fibers while still providing the threshold intensity. The material is not fragmented substantially beyond the illuminated region. The fragments which are generated are much finer than those obtained with the long pulse laser. The amount of material removed per pulse for a given fiber size is much lower for the high peak power laser than for the pulsed dye laser, so high repetition rates should be used.

Table II of optimized operating ranges has been assembled for the high peak power lasers.

TABLE I
Optimized Operating Range for a Pulsed Laser

|  | Urinary Calculi | Gallstones | Calcified Tissue |
|---|---|---|---|
| Fiber Diameter (low) | 60 microns | 60 microns | 60 microns |
| Fiber Diameter (high) | 600 microns | 600 microns | 600 microns |
| Fiber Diameter (optimum) | 200 microns | 200 microns | 200 microns |
| Color | 350 to 550 nm | 350 to 1100 nm prefer 600 to 1100 nm | 350 to 550 nm |
| Energy/Pulse (low) | 5 mj | 5 mj | 5 mj |
| Energy/Pulse (high) | 100 mj | 100 mj | 200 mj |
| Pulse Duration | .05 to 2 $\mu$sec | .05 to 2 $\mu$sec | .05 to 2 $\mu$sec |
| Rep Rate (single shot) | Desireable | Desireable | Desireable |
| Rep Rate (optimum) | 20 Hz | 20 Hz | 20 Hz |
| Intensity (low) | 5 MW/cm$^2$ | 5 MW/cm$^2$ | 5 MW/cm$^2$ |
| Intensity (high) | 400 MW/cm$^2$ | 400 MW/cm$^2$ | 400 MW/cm$^2$ |

TABLE II
Operating Range for a High Peak Power Pulsed Laser

|  | Urinary Calculi | Gallstones | Calcified Tissue |
|---|---|---|---|
| Fiber Diameter (low) | 200 microns | 200 microns | 200 microns |
| Fiber Diameter (high) | 1000 microns | 1000 microns | 1000 microns |
| Fiber Diameter (optimum) | 600 microns | 600 microns | 600 microns |
| Color | 350 to 550 nm | 350 to 1100 nm prefer 600 to 1100 nm | 350 to 550 nm |
| Peak Power for 600 Micron fiber (high) | 1 MW | 1 MW | 1 MW |
| Pulse Duration | 10 to 100 nsec prefer 50-100 nsec | 10 to 100 nsec prefer 50-100 nsec | 10 to 100 nsec prefer 50-100 nsec |
| Rep Rate | 100 Hz | 100 Hz | 100 Hz |
| Intensity (low) | 5 MW/cm$^2$ | 5 MW/cm$^2$ | 5 MW/cm$^2$ |
| Intensity (high) | 400 MW/cm$^2$ | 400 MW/cm$^2$ | 400 MW/cm$^2$ |

We claim:

1. Apparatus adapted for use in breaking down material for removal from within a body characterized in that it comprises:
   means for surrounding the material with liquid; and
   means for illuminating a localized region of the material using an optical fiber having a diameter between 60 microns and 600 microns and a pulsed laser of pulse duration between about 0.05 microsecond and 10 microseconds while the material is surrounded in liquid at such wavelengths and with energy per pulse between 5 millijoules and 200 millijoules and intensity at the localized region of at least 5 megawatts per square centimeter to cause in the operation of the apparatus fragmentation of the material without delivering energy sufficient to cause significant damage to other tissue in the vicinity of said material.

2. Apparatus as in claim 1, wherein the illuminating means is capable of generating a shockwave originating from within the localized region to cause fragmentation of the material substantially beyond the localized region.

3. Apparatus as claimed in claim 1, wherein the illuminating means comprises optical fiber through which the localized region is illuminated in the operation of the apparatus.

4. Apparatus as claimed in claim 3, wherein the distal end of the optical fiber is adapted to be placed in contact with or very near to the localized region of the material.

5. Apparatus as claimed in claim 1, wherein the pulsed laser is a dye laser.

6. Apparatus as claimed in claim 1, wherein the pulsed laser is arranged for a pulse duration between 0.05 microsecond and 2 microseconds.

7. Apparatus as claimed in claim 6 wherein the pulsed laser is arranged for a pulse duration greater than 0.1 microsecond.

8. Apparatus as claimed in claim 6 wherein the pulsed laser is adapted to apply pulse bursts to the material to fragment the material and, thereafter, single pulses to individual fragments to further break up the material.

9. Apparatus as claimed in claim 8 wherein the pulsed laser is capable of a repetition rate of the pulse bursts greater than 10 Hertz.

10. Apparatus as claimd in claim 6 wherein the laser light has a wavelength between 350 nanometers and 550 nanometers.

11. Apparatus adapted for use in breaking down material for removal from within a body characterized in that it comprises:
    means for surrounding the material with liquid;
    means for positioning the distal end of optical fiber against or very near to a localized region of the material; and
    means for illuminating the localized region of the material with a pulsed laser through the optical fiber at a wavelength and with energy per pulse between 5 millijoules and 200 millijoules and intensity at the localized region of at least 5 megawatts per square centimeter to cause in the operation of the apparatus a shockwave originating against or very near the material and to fragment the material beyond the localized region.

12. Apparatus as claimed in claim 11 wherein the pulsed laser is arranged for a pulse duration of between 0.05 and 2 microseconds.

13. Apparatus as claimed in claim 11, wherein the pulsed laser is a dye laser.

14. A method of breaking down material for removal from within a body comprising:
    surrounding the material with a liquid; and illuminating a localized region of the material with a pulsed laser through fiber optics solely while the material is surrounded with liquid at such wavelengths and with energy per pulse between 5 millijoules and 200 millijoules and intensity at the localized region of at least 5 megawatts per square centimeter to cause shockwave fragmentation of the material, fragmentation being due principally to the shockwave, without delivering energy sufficient to cause significant damage to other tissue in the vicinity of said material.

15. A method as claimed in claim 14 wherein the localized region is illuminated through optical fiber.

16. A method as claimed in claim 15 wherein the distal end of the optical fiber is placed in contact with or very near to the localized region of the material.

17. A method as claimed in claim 14 wherein the pulsed laser is a dye laser.

18. A method as claimed in claim 14, wherein the pulse duration of the pulse laser is between 0.05 microsecond and 2 microseconds.

19. A method as claimed in claim 18 wherein the pulse duration is greater than 0.1 microsecond.

20. A method as claimed in claim 18 wherein the optical fiber has a diameter of between 60 microns and 600 microns.

21. A method as claimed in claim 18 wherein pulse bursts from the pulsed laser are applied to the material to fragment the material and, thereafter, single pulses are applied to individual fragments to further break up the material.

22. A method as claimed in claim 21 wherein the repetition rate of the pulse bursts is greater than 10 hertz.

23. A method as claimed in claim 18 for fragmenting urinary calculi wherein the laser light has a wavelength between 350 nanometers and 550 nanometers.

24. A method of breaking down material for removal from within a body comprising:
surrounding the material with liquid;
positioning the distal end of optical fiber having a diameter less than 600 microns against or very near to a localized region of the material; and
illuminating the localized region of the material with a pulsed laser having pulse duration in the order of microseconds through the optical fiber at a wavelength and with energy per pulse between 5 millijoules and 200 millijoules and intensity at the localized region of at least 5 megawatts per square centimeter to cause a shockwave originating at or near the localized region to fragment the material beyond the localized region.

25. A method as claimed in claim 24 wherein the pulse duration is between 0.05 microsecond and 2 microseconds.

26. A method as claimed in claim 25 wherein the energy per pulse from the pulsed laser is between 5 millijoules and 200 millijoules and the pulse duration is between 0.1 microsecond and 2 microseconds.

27. A method as claimed in claim 25 wherein the optical fiber has a diameter between 60 microns and 600 microns.

28. A method as claimed in claim 24, wherein the pulsed laser is a dye laser.

29. A method for breaking down a calculus, stone, or other calcified tissue within a body comprising:
a. inserting an optical fiber of diameter less than about 600 microns into the body to a position sufficient for the distal end of the fiber to directly illuminate the calculus, stone, or calcified tissue;
b. exposing the calculus, stone, or calcified tissue and surrounding liquid to laser light having energy per pulse between 5 millijoules and 200 millijoules and intensity of at least 5 megawatts per square centimeter and pulse duration and wavelength characteristics sufficient to initiate fragmentation of the calcified tissue with production of an acoustic signal within the calcified tissue.

30. A method of claim 29, wherein the laser has a characteristic wavelength of about 350 to 500 nanometers.

31. A method of claim 29, wherein the laser pulses are derived from a pulsed dye laser having a pulse duration in the order of microseconds.

32. A method of claim 31, wherein the laser pulses have a duration of between 0.05 and 2 microseconds.

33. A method of claim 29, wherein the laser pulses are those of an Excimer laser having a pulse duration of at least 10 nanoseconds.

34. A method of destroying a target for removal from within a body, comprising:
a. inserting an optical fiber of diameter less than about 600 microns into the body so that the distal end of the fiber can directly illuminate both the target to be destroyed and liquid surrounding the target;
b. triggering a shockwave within the target through application of pulsed laser light having energy per pulse between 5 millijoules and 200 millijoules and intensity of at least 5 megawatts per square centimeter to the target via the optical fiber to cause shockwave fragmentation of the target so that at least some fraction of the target is fragmented and none of the surrounding, non-targetted tissue is fragmented.

35. A method of claim 34, wherein the pulsed laser has a duration of between 0.05 and 2 microseconds and a wavelength of between 350 and 550 nanometers.

* * * * *

UNITED STATES PATENT AND TRADEMARK OFFICE
CERTIFICATE OF CORRECTION

PATENT NO.   :  4,887,600
DATED        :  December 19, 1989
INVENTOR(S)  :  Graham Watson and Horace Furumoto It is certified that error appears in the above-identified patent and that said Letters Patent is hereby corrected as shown below:

Title Page:

Add the second assignee as follows:

---Candela Laser Corporation, Wayland, Massachusetts---

Signed and Sealed this

Twenty-first Day of January, 1992

*Attest:*

HARRY F. MANBECK, JR.

*Attesting Officer*  *Commissioner of Patents and Trademarks*